(12) United States Patent
Wang (10) Patent No.: US 10,265,866 B2
(45) Date of Patent: Apr. 23, 2019

(54) SPHERICAL LINKAGE TYPE SURGICAL ROBOTIC ARM

(71) Applicant: HIWIN TECHNOLOGIES CORP., Taichung (TW)

(72) Inventor: Ren-Jeng Wang, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 354 days.

(21) Appl. No.: 15/367,812

(22) Filed: Dec. 2, 2016

(65) Prior Publication Data

US 2017/0120456 A1 May 4, 2017

Related U.S. Application Data

(62) Division of application No. 13/923,670, filed on Jun. 21, 2013, now abandoned.

(51) Int. Cl.
*A61B 34/30* (2016.01)
*B25J 17/00* (2006.01)
*F16H 21/54* (2006.01)

(52) U.S. Cl.
CPC .............. *B25J 17/00* (2013.01); *A61B 34/30* (2016.02); *F16H 21/54* (2013.01); *Y10S 901/21* (2013.01); *Y10S 901/28* (2013.01)

(58) Field of Classification Search
CPC .......................... A61B 19/2203; A61B 34/30
See application file for complete search history.

(56) References Cited

U.S. PATENT DOCUMENTS

| | | | | |
|---|---|---|---|---|
| 5,046,375 | A * | 9/1991 | Salisbury, Jr. ........... | B25J 9/046 414/7 |
| 6,355,048 | B1 * | 3/2002 | Hong ..................... | A61B 90/50 606/107 |
| 7,209,228 | B2 * | 4/2007 | Li ....................... | A61C 13/0004 356/244 |
| 2005/0119638 | A1 * | 6/2005 | Jensen ................... | B25J 9/1065 606/1 |
| 2006/0243085 | A1 * | 11/2006 | Hannaford ........... | B25J 17/0266 74/490.01 |
| 2007/0089557 | A1 * | 4/2007 | Solomon ................ | B25J 9/1045 74/490.01 |
| 2007/0173976 | A1 | 7/2007 | Schena | |
| 2007/0173977 | A1 * | 7/2007 | Schena ................ | B25J 17/0258 700/263 |
| 2009/0234369 | A1 * | 9/2009 | Bax ..................... | A61B 17/3403 606/130 |
| 2012/0184968 | A1 * | 7/2012 | Schena .................. | A61B 34/37 606/130 |

* cited by examiner

*Primary Examiner* — Julie A Szpira
(74) *Attorney, Agent, or Firm* — Muncy, Geissler, Olds & Lowe, P.C.

(57) ABSTRACT

In order to reduce the calculation in robotic arm allocation, the invention provides a spherical linkage type surgical robotic arm, which includes a first curved bar having a first axis center and a second axis center, a second curved bar being equal to the first curved bar in length and having a third axis center and a fourth axis center, the third axis center in coincidence with the first axis center, a third curved bar having a fifth axis center and a sixth axis center and being pivoted to the second curved bar, and a fourth curved bar having a seventh axis center and an eighth axis center and being pivoted to the third curved bar and the first curved bar, thereby reducing the calculation burden and facilitating control and allocation.

6 Claims, 7 Drawing Sheets

SPHERICAL LINKAGE TYPE SURGICAL ROBOTIC ARM

CROSS REFERENCE TO RELATED APPLICATIONS

This application is a Divisional of co-pending application Ser. No. 13/923,670, filed on 21 Jun. 2013, for which priority is claimed under 35 U.S.C. §120; and the entire contents of all of which are hereby incorporated by reference.

BACKGROUND OF THE INVENTION

1. Field of the Invention

The present invention relates to robots and more particularly, to a spherical linkage type surgical robotic arm.

2. Description of the Related Art

With the advances in medical technology, new surgical techniques have been continuously introduced. Fast and low risk surgical techniques that enable patients to recover faster have been the goal of the medical profession, and the very popular minimally invasive surgery in recent years is one of them. For example, endoscopic imaging technology and micro-surgical instruments are used in laparoscopic surgery, so that the surgery can be performed without making a large wound on the body of the patient, not only reducing blood loss in the patient but also enabling the body of the patient to recover quickly from the wound.

However, when performing a laparoscopic surgery, the surgeon needs to insert an endoscopic imaging module and a surgical instrument module into the body of the patient and then to perform the surgery while simultaneously viewing the endoscopic image. Thus, the surgeon will need the assist of a mechanical arm to hold or operate the related surgical instruments so that the surgeon can proceed with the operation.

Conventional robotic arms commonly have a complicated structure and require complicated calculations and precise control to achieve precise allocation. US 2007/0173976 A1 discloses a center robotic arm with five-bar spherical linkage for endoscopic camera. According to this design, each link has a different length (see FIG. 7A and FIG. 7B), therefore, it requires a large amount of calculations to precisely move the outward axis to the desired location.

Further, US2012/0184968 discloses a robotic arm with five-bar spherical linkage, which uses a parallel spherical five-bar linkage. According to this design, the surgical instrument is affixed to an extension portion of one link (see FIG. 15). This designs allows the surgical instrument to pass through the center of spherical rotation, however the other part beyond the center of spherical rotation will be turned with the respective link around the center of spherical rotation. During movement of the link, the large turning angle of the surgical instrument will reduce the readability for the surgeon to read the data being displayed on the surface of the surgical instrument.

SUMMARY OF THE INVENTION

The present invention has been accomplished under the circumstances in view. It is the main object of the present invention to provide a spherical linkage type surgical robotic arm, which reduces calculation burden by uniformizing link length, achieving better robotic arm control and allocation than conventional robotic arm designs.

It is another object of the present invention to provide a spherical linkage type surgical robotic arm, which has an added instrument bar that provides a turn proportional relationship relative to the links so that the turning angle of the surgical instrument mounted at the instrument bar can be reduced, bringing to the surgeon better readability of the data being displayed on surface of the surgical instrument than conventional mechanical arm designs.

To achieve these and other objects of the present invention, a spherical linkage type surgical robotic arm turnable around a center of spherical rotation in accordance with the present invention comprises a first curved bar, which comprises a first axis center and a second axis center respectively located at two opposite ends thereof and passed through the center of spherical rotation; a second curved bar, which is equal to the first curved bar in length, comprising a third axis center and a fourth axis center respectively located at two opposite ends thereof and passed through the center of spherical rotation, the third axis center coincides with the first axis center; a third curved bar, which comprises a fifth axis center and a sixth axis center respectively located at two opposite ends thereof and passed through the center of spherical rotation, the third curved bar being pivotally connected to the second curved bar in such a manner that the fifth axis center coincides with the fourth axis center; and a fourth curved bar, which comprises a seventh axis center and an eighth axis center respectively located at two opposite ends thereof and passed through the center of spherical rotation, the fourth curved bar being respectively pivotally connected to the third curved bar and the first curved bar in such a manner that the seventh axis center coincides with the sixth axis center and the eighth axis center coincides with the second axis center.

Subject to the design that the first curved bar and the second curved bar have the same length, the calculation conditions are simplified, and therefore the calculation burden can be reduced, achieving easier robotic arm control and allocation than conventional robotic arm designs.

Further, the invention also provides a spherical linkage type surgical robotic arm turnable around a center of spherical rotation, comprising a first curved bar, which comprises a first axis center and a second axis center respectively located at two opposite ends thereof and passed through the center of spherical rotation; a second curved bar, which comprises a third axis center and a fourth axis center respectively located at two opposite ends thereof and passed through the center of spherical rotation, the third axis center coincides with the first axis center; a third curved bar, which comprises a fifth axis center and a sixth axis center respectively located at two opposite ends thereof and passed through the center of spherical rotation, the third curved bar being pivotally connected to the second curved bar in such a manner that the fifth axis center coincides with the fourth axis center; a fourth curved bar, which comprises a seventh axis center and an eighth axis center respectively located at two opposite ends thereof and passed through the center of spherical rotation, the fourth curved bar being respectively pivotally connected to the third curved bar and the first curved bar in such a manner that the seventh axis center coincides with the sixth axis center and the eighth axis center coincides with the second axis center; an instrument bar, which comprises an operational axis center passed through the center of spherical rotation, the instrument bar being pivotally connected to the third curved bar or the fourth curved bar such that the operational axis center coincides with the sixth axis center or the seventh axis center; a first proportional wheel fixedly mounted at the first curved bar to let the second axis center pass through the wheel axle center of the first proportional wheel; a second proportional wheel having a diameter larger than the diameter of the first proportional wheel, the second proportional wheel being fixedly mounted at the instrument bar to let the operational axis center pass through the wheel axle center of the second proportional wheel; and a flexible element wound round the first proportional wheel and the second proportional wheel.

Subject to the arrangement of the instrument bar for the mounting of a surgical instrument and the arrangement of the first proportional wheel and the second proportional wheel, there is a turn proportional relationship between the instrument bar and the other curved bars so that the turning angle of the surgical instrument at the instrument bar can be reduced, bringing to the surgeon better readability of the data being displayed on the surface of the surgical instrument than conventional mechanical arm designs.

Based on the same spirit of the invention, the invention also provides a spherical linkage type surgical robotic arm turnable around a center of spherical rotation, comprising: a first curved bar, which comprises a first axis center and a second axis center respectively located at two opposite ends thereof and passed through the center of spherical rotation; a second curved bar, which comprises a third axis center and a fourth axis center respectively located at two opposite ends thereof and passed through the center of spherical rotation; a third curved bar, which comprises a fifth axis center and a sixth axis center respectively located at two opposite ends thereof and passed through the center of spherical rotation, the third curved bar being pivotally connected to the second curved bar in such a manner that the fifth axis center coincides with the fourth axis center; a fourth curved bar, which comprises a seventh axis center and an eighth axis center respectively located at two opposite ends thereof and passed through the center of spherical rotation, the fourth curved bar being respectively pivotally connected to the third curved bar and the first curved bar in such a manner that the seventh axis center coincides with the sixth axis center and the eighth axis center coincides with the second axis center; a ground bar, which comprises a ninth axis center and a tenth axis center respectively located at two opposite ends thereof and passed through the center of spherical rotation, the ninth axis center coincides with the first axis center and the tenth axis center coincides with the third axis center; an instrument bar, which comprises an operational axis center passed through the center of spherical rotation, the instrument bar being pivotally connected to the third curved bar or the fourth curved bar such that the operational axis center coincides with the sixth axis center or the seventh axis center; a first proportional wheel fixedly mounted at the first curved bar to let the second axis center pass through the wheel axle center of the first proportional wheel; a second proportional wheel having a diameter larger than the diameter of the first proportional wheel, the second proportional wheel being fixedly mounted at the instrument bar to let the operational axis center pass through the wheel axle center of the second proportional wheel; and a flexible element wound round the first proportional wheel and the second proportional wheel.

Subject to the arrangement of the instrument bar for the mounting of a surgical instrument and the arrangement of the first proportional wheel and the second proportional wheel, there is a turn proportional relationship between the instrument bar and the other curved bars so that the turning angle of the surgical instrument at the instrument bar can be reduced, bringing to the surgeon better readability of the data being displayed on the surface of the surgical instrument than conventional mechanical arm designs.

Other advantages and features of the present invention will be fully understood by reference to the following specification in conjunction with the accompanying drawings, in which like reference signs denote like components of structure.

DETAILED DESCRIPTION OF THE INVENTION

Figure 1:
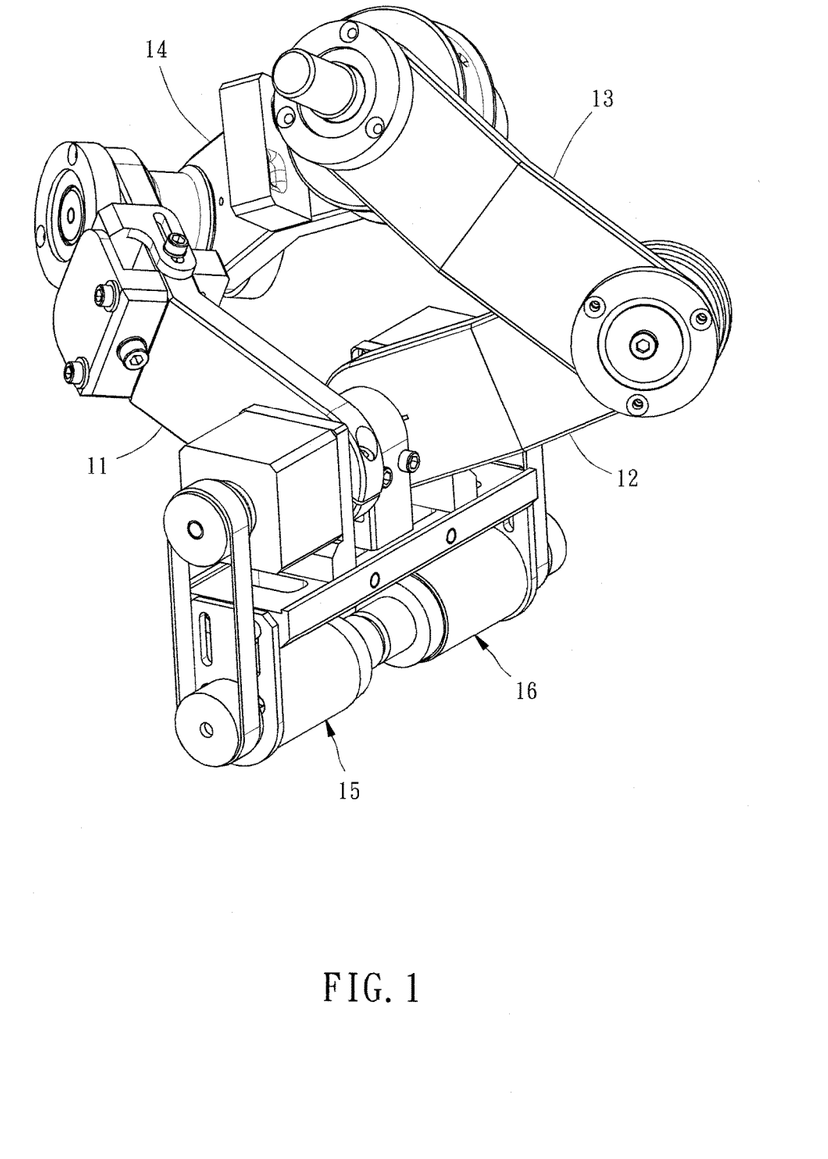
FIG. 1 is an elevational view of a spherical linkage type surgical robotic arm in accordance with a first embodiment of the present invention.
Figure 2:
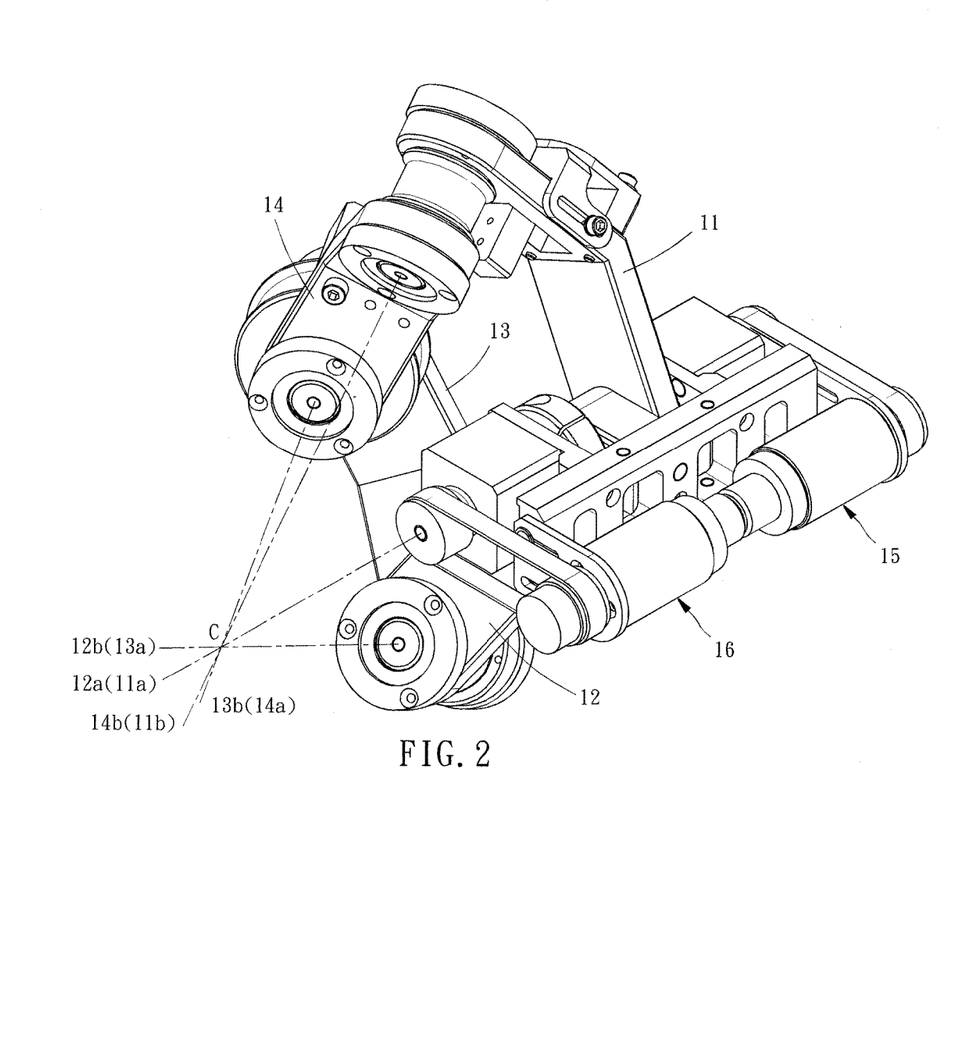
FIG. 2 is an elevational view of the spherical linkage type surgical robotic arm in accordance with the first embodiment of the present invention when viewed from another angle.
Figure 3:
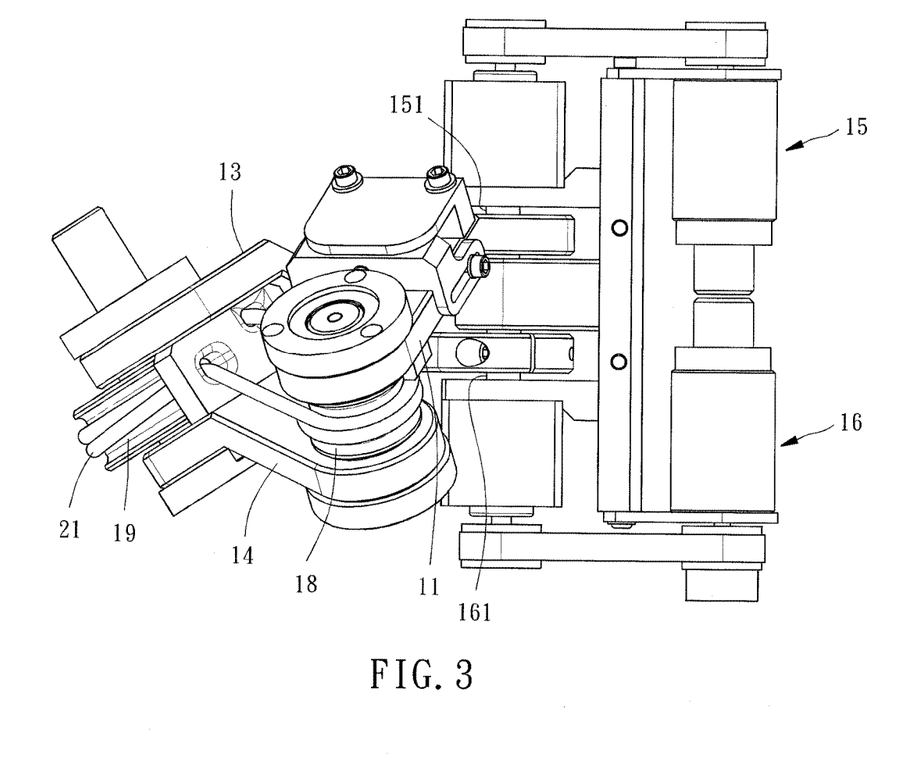
FIG. 3 is a side view of the spherical linkage type surgical robotic arm in accordance with the first embodiment of the present invention.

Referring to FIGS. 1-3, a spherical linkage type surgical robotic arm in accordance with a first embodiment of the present invention is shown turnable around a center of spherical rotation C. The spherical linkage type surgical robotic arm comprises a first curved bar 11, a second curved bar 12, a third curved bar 13 and a fourth curved bar 14.

It is to be noted that the axle center described in this specification is a virtual axis about which an object is turned.

The first curved bar 11 has a first axis center 11a and a second axis center 11b respectively located at two opposite ends thereof and passed through the center of spherical rotation C.

The second curved bar 12 is of equal length relative to the first curved bar 11, having a third axis center 12a and a fourth axis center 12b respectively located at two opposite ends thereof and passed through the center of spherical rotation C. Further, the third axis center 12a coincides with the first axis center 11a.

The third curved bar 13 has a fifth axis center 13a and a sixth axis center 13b respectively located at two opposite ends thereof and passed through the center of spherical rotation C. The third curved bar 13 is pivotally connected to the second curved bar 12. Further, the fifth axis center 13a coincides with the fourth axis center 12b.

The fourth curved bar 14 has a seventh axis center 14a and an eighth axis center 14b respectively located at two opposite ends thereof and passed through the center of spherical rotation C. The fourth curved bar 14 is respectively pivotally connected to the third curved bar 13 and the first curved bar 11. The seventh axis center 14a coincides with the sixth axis center 13b. The eighth axis center 14b coincides with the second axis center 11b.

In addition to the condition that the first curved bar 11 and the second curved bar 12 have the same length, the third curved bar 13 and the fourth curved bar 14 can be made having the same length, simplifying the program operation in controlling the motion of every curved bar in the preferred embodiments of the present invention. More particularly, the second curved bar 12 and the third curved bar 13 can be made having the same length. In this embodiment, the first curved bar 11, the second curved bar 12, the third curved bar 13 and the fourth curved bar 14 have the same length, further reducing the calculation burden and shortening the calculation time.

In this embodiment, the spherical linkage type surgical robotic arm further comprises a first driving mechanism 15 and a second driving mechanism 16. The first driving mechanism 15 is a combination of a motor and a speed reducer for driving an object to rotate, comprising a first driving shaft 151 connected to the first curved bar 11 and coincided with the first axis center 11a. The second driving mechanism 16 comprises a second driving shaft 161 connected to the second curved bar 12 and coincided with the third axis center 12a. Because the first driving shaft 151 and the second driving shaft 161 are respectively and directly connected to the first curved bar 11 and the second curved bar 12, the number of component parts can be relatively reduced, thereby reducing the manufacturing cost and shortening the assembling time, and therefore the invention is cost-effective. Further, through the first driving mechanism 15 and the second driving mechanism 16 to control relative motion between the first curved bar 11 and the second curved bar 12, the motion of the spherical linkage type surgical robotic arm is thus controlled.

It is to be noted that the curved bar length indicated herein means the shortest distance between the two centers of axis of each curved bar at the common sphere based on the center of spherical rotation C.

Figure 4:
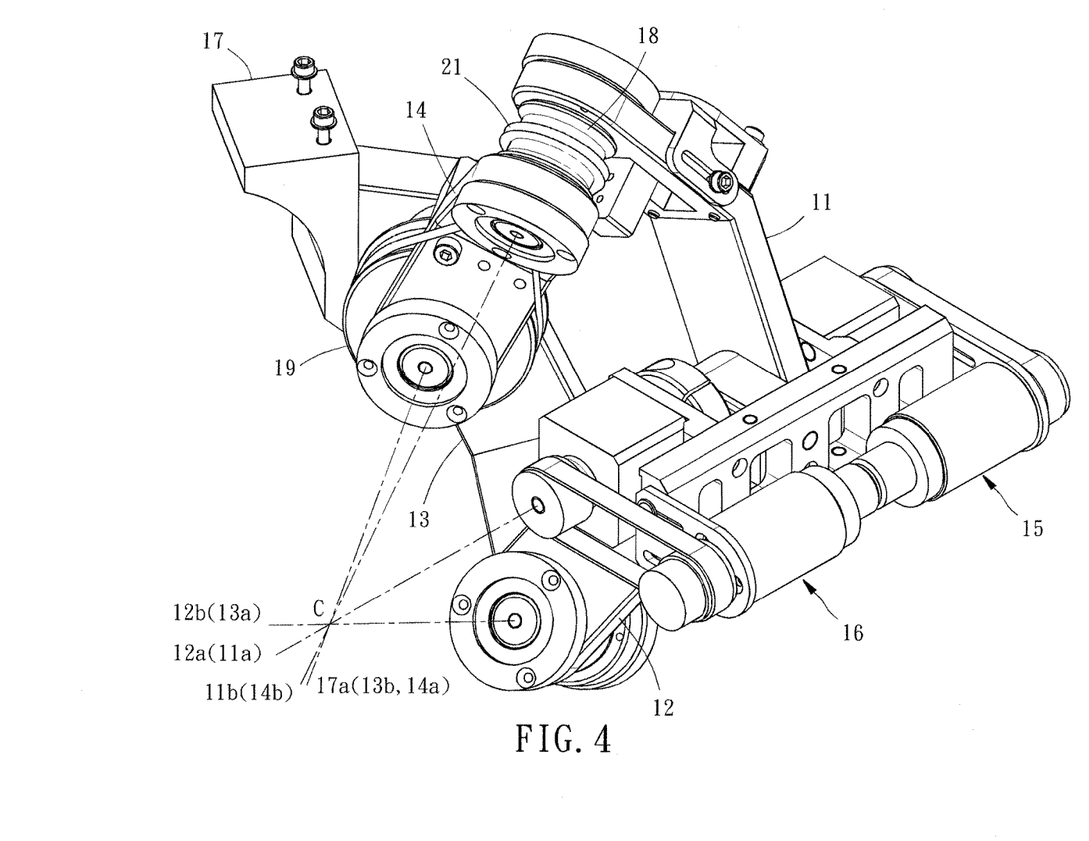
FIG. 4 is an elevational view of a spherical linkage type surgical robotic arm in accordance with a second embodiment of the present invention.
Figure 5:
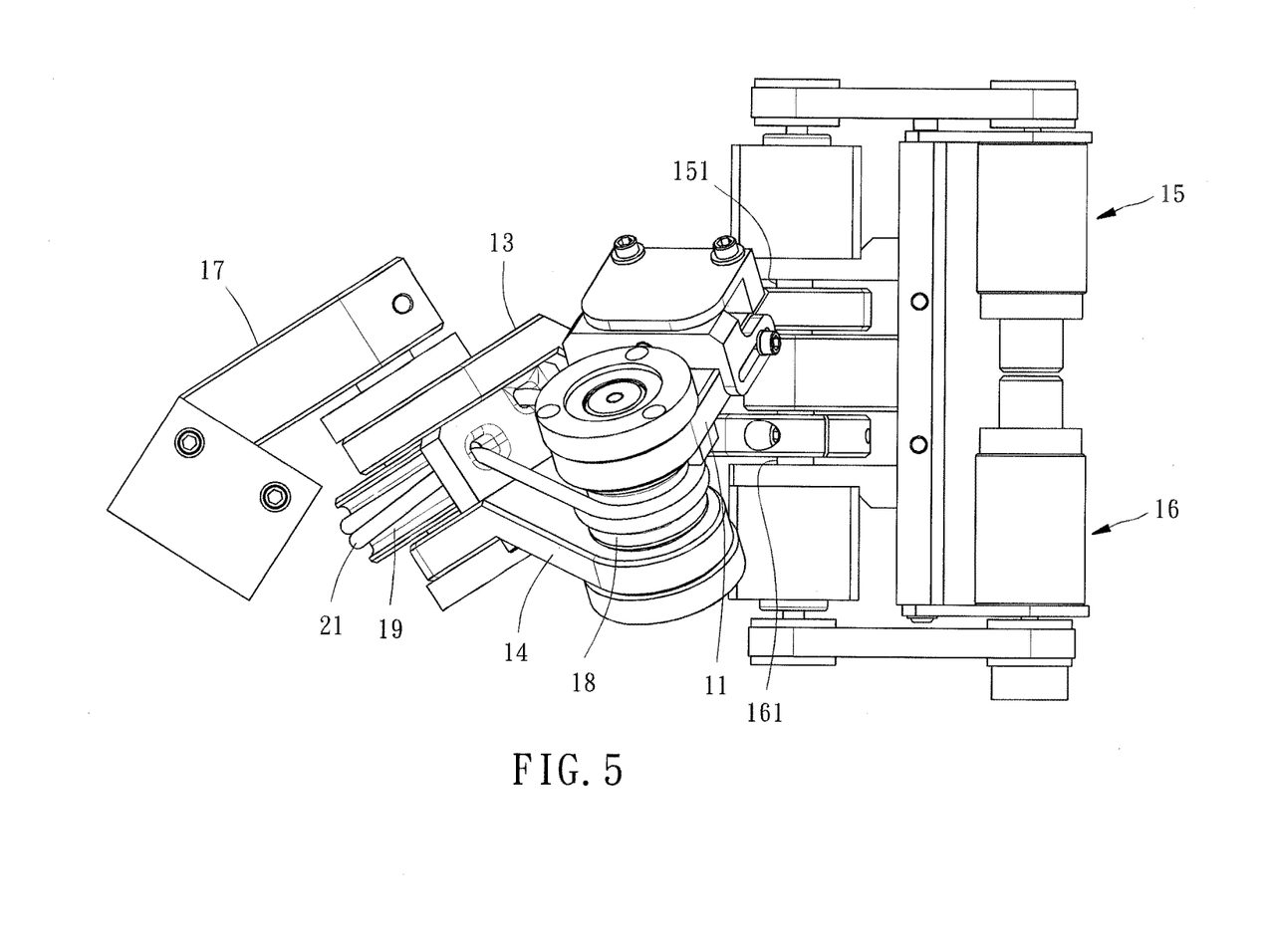
FIG. 5 is a side view of the spherical linkage type surgical robotic arm in accordance with the second embodiment of the present invention.
Figure 6:
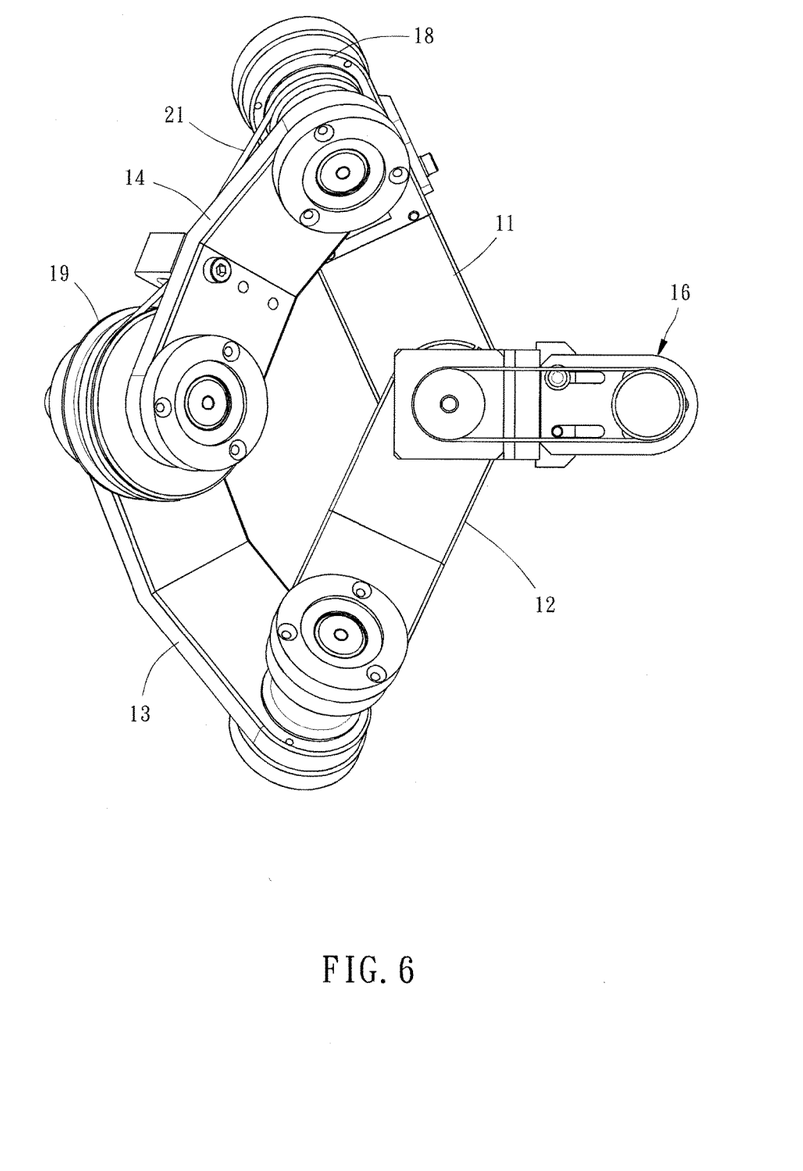
FIG. 6 is a bottom view of the spherical linkage type surgical robotic arm in accordance with the second embodiment of the present invention.

Referring to FIGS. 4 and 5, a spherical linkage type surgical robotic arm in accordance with a second embodiment of the present invention is shown. This second embodiment is substantially similar to the aforesaid first embodiment with the exception that this second embodiment further comprises an instrument bar 17, a first proportional wheel 18, a second proportional wheel 19, and a flexible element 21.

The instrument bar 17 comprises an operational axis center 17a passed through the center of spherical rotation C. The instrument bar 17 is pivotally connected to the third curved bar 13 or fourth curved bar 14. Further, the operational axis center 17a coincides with the sixth axis center 13b or seventh axis center 14a.

The first proportional wheel 18 is fixedly connected to the first curved bar 11 and rotatable with the first curved bar 11 to let the second axis center 11b pass through the wheel axle center of the first proportional wheel 18.

The diameter of the second proportional wheel 19 is larger than the diameter of the first proportional wheel 18. Further, the second proportional wheel 19 is fixedly connected to the instrument bar 17 and rotatable with the instrument bar 17 to let the operational axis center 17a pass through the wheel axle center of the second proportional wheel 19.

The flexible element 21 is wound round the first proportional wheel 18 and the second proportional wheel 19. In this embodiment, the flexible element 21 is a steel wire rope. However, this is not a limitation. It can also be a rope or belt.

In this embodiment, installation of the first proportional wheel 18, the second proportional wheel 19 and the flexible element 21 achieves the effect of enabling the turning angle of the instrument bar 17 to be smaller than the turning angle of the fourth curved bar 14 without the condition of having the first curved bar 11 and the second curved bar 12 to be made equal in length. However, if the first curved bar 11 and the second curved bar 12 have the same length, it achieves the effect of shortening the calculation time. Further, the second curved bar 12 and the third curved bar 13 can also be made equal in length, enhancing the effects.

If the diameter of the second proportional wheel 19 is twice the diameter of the first proportional wheel 18 under the condition that the first curved bar 11, the second curved bar 12, the third curved bar 13 and the fourth curved bar 14 have the same length, the contained angle between the instrument bar 17 and the third curved bar 13 and the contained angle between the instrument bar 17 and the fourth curved bar 14 can be kept equal.

During the operation of the second embodiment of the present invention, due to the installation of the first proportional wheel 18 and the second proportional wheel 19, there is a turn proportional relationship between the instrument bar 17 and the first curved bar 11, and therefore the turning angle of the surgical instrument mounted at the instrument bar 17 can be reduced, bringing to the surgeon better readability of the data being displayed on the surface of the surgical instrument than conventional mechanical arm designs.

Figure 7:
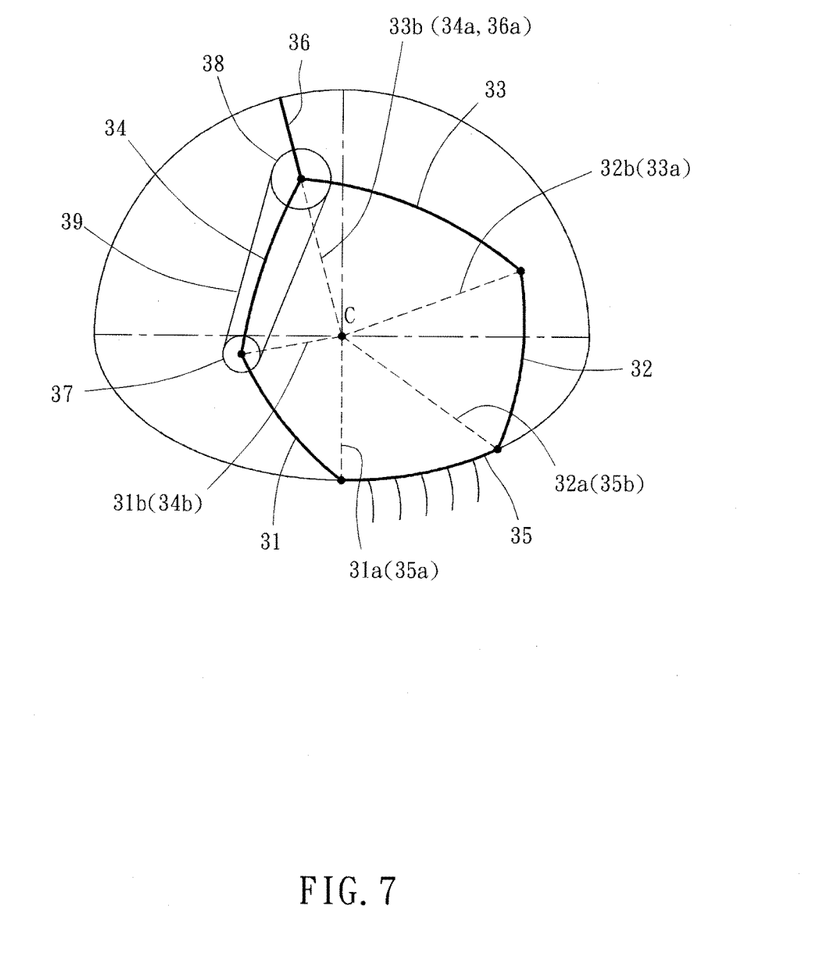
FIG. 7 is a schematic perspective view of a spherical linkage type surgical robotic arm in accordance with a third embodiment of the present invention.

Referring to FIG. 7, a spherical linkage type surgical robotic arm in accordance with a third embodiment of the present invention is shown turnable about a center of spherical rotation. The spherical linkage type surgical robotic arm comprises: a first curved bar 31, a second curved bar 32, a third curved bar 33, a fourth curved bar 34, a ground bar 35, an instrument bar 36, a first proportional wheel 37, a second proportional wheel 38 and a flexible element 39.

The first curved bar 31 has a first axis center 31a and a second axis center 31b respectively located at two opposite ends thereof and passed through the center of spherical rotation C.

The second curved bar 32 has a third axis center 32a and a fourth axis center 32b respectively located at two opposite ends thereof and passed through the center of spherical rotation C.

The third curved bar 33 has a fifth axis center 33a and a sixth axis center 33b respectively located at two opposite ends thereof and passed through the center of spherical rotation C. The third curved bar 33 is pivotally connected to the second curved bar 32. Further, the fifth axis center 33a coincides with the fourth axis center 32b.

The fourth curved bar 34 has a seventh axis center 34a and an eighth axis center 34b respectively located at two opposite ends thereof and passed through the center of spherical rotation C. The fourth curved bar 34 is respectively pivotally connected to the third curved bar 33 and the first curved bar 31. The seventh axis center 34a coincides with the sixth axis center 33b. The eighth axis center 34b coincides with the second axis center 31b.

The ground bar 35 has a ninth axis center 35a and a tenth axis center 35b respectively located at two opposite ends thereof and passed through the center of spherical rotation C. Further, said ninth axis center 35a being coincided with said first axis center 31a, and the tenth axis center 35b coincides with the third axis center 32b.

The instrument bar 36 comprises an operational axis center 36a passed through the center of spherical rotation C. The instrument bar 36 is pivotally connected to the third curved bar 33 or fourth curved bar 34. Further, the operational axis center 36a coincides with the sixth axis center 33b or seventh axis center 34a.

The first proportional wheel 37 is fixedly connected to the first curved bar 31 and rotatable with the first curved bar 31 to let the second axis center 31b pass through the wheel axle center of the first proportional wheel 37.

The diameter of the second proportional wheel 38 is larger than the diameter of the first proportional wheel 37. Further, the second proportional wheel 38 is fixedly connected to the instrument bar 36 and rotatable with the instrument bar 36 to let the operational axis center 36a pass through the wheel axle center of the second proportional wheel 38.

The flexible element 39 is wound round the first proportional wheel 37 and the second proportional wheel 38. In this embodiment, the flexible element 39 is a steel wire rope. However, this is not a limitation. It can also be a rope or belt.

In this embodiment, in addition to the condition that the first curved bar 31 and the second curved bar 32 have the same length, the third curved bar 33 and the fourth curved bar 34 can also be made having the same length to simplify the calculation in controlling the motion of each curved bar. More particularly, the second curved bar 32 and the third curved bar 33 can be made having the same length. For example, in this embodiment, the first curved bar 31, the second curved bar 32, the third curved bar 33 and the fourth curved bar 34 have the same length, further reducing the calculation burden and shortening the calculation time. Further, due to the installation of the first proportional wheel 37 and the second proportional wheel 38, there is a turn proportional relationship between the instrument bar 36 and the first curved bar 37, and therefore the turning angle of the surgical instrument mounted at the instrument bar 36 can be reduced, bringing to the surgeon better readability of the data displayed on the surface of the surgical instrument when compared to conventional mechanical arm designs.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A spherical linkage type surgical robotic arm turnable around a center of spherical rotation, comprising:

a first curved bar comprising a first axis center and a second axis center respectively located at two opposite ends thereof and passed through said center of spherical rotation;

a second curved bar comprising a third axis center and a fourth axis center respectively located at two opposite ends thereof and passed through said center of spherical rotation, said third axis center being coincided with said first axis center;

a third curved bar comprising a fifth axis center and a sixth axis center respectively located at two opposite ends thereof and passed through said center of spherical rotation, said third curved bar being pivotally connected to said second curved bar, said fifth axis center being coincided with said fourth axis center;

a fourth curved bar comprising a seventh axis center and an eighth axis center respectively located at two opposite ends thereof and passed through said center of spherical rotation, said fourth curved bar being respectively pivotally connected to said third curved bar and said first curved bar, said seventh axis center being coincided with said sixth axis center, said eighth axis center being coincided with said second axis center;

an instrument bar comprising an operational axis center passed through said center of spherical rotation, said instrument bar being pivotally connected to one of said third curved bar and said fourth curved bar, said operational axis center being coincided with one of said sixth axis center and said seventh axis center;

a first proportional wheel fixedly mounted at said first curved bar to let said second axis center pass through said wheel axle center of said first proportional wheel;

a second proportional wheel having a diameter larger than the diameter of said first proportional wheel, said second proportional wheel being fixedly mounted at said instrument bar to let said operational axis center pass through said wheel axle center of said second proportional wheel; and a flexible element wound round said first proportional wheel and said second proportional wheel.

2. The spherical linkage type surgical robotic arm as claimed in claim 1, wherein said first curved bar and said second curved bar are equal in length.

3. The spherical linkage type surgical robotic arm as claimed in claim 2, wherein said third curved bar and said fourth curved bar are equal in length.

4. The spherical linkage type surgical robotic arm as claimed in claim 3, wherein said second curved bar and said third curved bar are equal in length.

5. The spherical linkage type surgical robotic arm as claimed in claim 4, wherein the diameter of said second curved bar is twice the diameter of said first curved bar.

6. The spherical linkage type surgical robotic arm as claimed in claim 1, further comprising a first driving mechanism, said first driving mechanism comprising a first driving shaft connected to said first curved bar and coincided with said first axis center, and a second driving mechanism, said second driving mechanism comprising a second driving shaft connected to said second curved bar and coincided with said third axis center.

* * * * *